(12) United States Patent
Kronstedt et al.

(10) Patent No.: US 11,051,757 B2
(45) Date of Patent: Jul. 6, 2021

(54) SELF-ALIGNING DEVICE TO PATCH INTERFACE

(71) Applicant: Preventice Technologies, Inc., Rochester, MN (US)

(72) Inventors: Brian Walter Kronstedt, Shoreview, MN (US); Timothy Jon Alpers, Rochester, MN (US); Charles Rector, Edina, MN (US)

(73) Assignee: Preventice Technologies, Inc., Rochester, MN (US)

( * ) Notice: Subject to any disclaimer, the term of this patent is extended or adjusted under 35 U.S.C. 154(b) by 0 days.

(21) Appl. No.: 16/264,157

(22) Filed: Jan. 31, 2019

(65) Prior Publication Data
US 2020/0245936 A1 Aug. 6, 2020

(51) Int. Cl.
*A61B 5/28* (2021.01)
*A61B 5/00* (2006.01)
*A43B 3/00* (2006.01)

(52) U.S. Cl.
CPC .......... *A61B 5/6807* (2013.01); *A43B 3/0005* (2013.01); *A61B 5/6833* (2013.01); *A61B 5/6835* (2013.01)

(58) Field of Classification Search
CPC . A61B 5/04085; A61B 5/0006; A61B 5/0402; A61B 5/0245; A61B 5/04012; A61B 5/0404; A61B 5/02438; A61B 5/6831; A61B 5/0428; A61B 5/0422; A61B 2560/0412; A61B 5/04087; A61B 5/6804; A61B 5/6833; A61B 5/024; A61B 5/681; A61B 5/6814
USPC ..................... 600/372, 382–393, 508–509
See application file for complete search history.

(56) References Cited

U.S. PATENT DOCUMENTS

| 6,605,046 B1 * | 8/2003 | Del Mar ............ A61B 5/04085 600/507 |
| 8,747,363 B2 * | 6/2014 | Nielsen ............. A61M 5/14248 604/180 |
| 9,579,021 B2 * | 2/2017 | Chang .................. A61B 5/6838 |
| 2008/0139953 A1 * | 6/2008 | Baker .................. A61B 5/0006 600/509 |
| 2008/0288026 A1 * | 11/2008 | Cross ..................... H01R 13/24 607/60 |

(Continued)

FOREIGN PATENT DOCUMENTS

| EP | 2906102 A2 | 8/2015 |
| GB | 2368127 A | 4/2002 |

OTHER PUBLICATIONS

PCT Notification of Transmittal of The International Search Report and the Written Opinion of the International Searcching Authority, or the Declaration for Application No. PCT/US2019/27957 dated Feb. 28, 2020.

*Primary Examiner* — Joseph A Stoklosa
*Assistant Examiner* — Brian M Antiskay
(74) *Attorney, Agent, or Firm* — Patterson + Sheridan, LLP

(57) ABSTRACT

Embodiments described herein relate to apparatus and techniques for aligning and coupling a sensor device to a wearable patch. A shoe apparatus is coupled to the wearable patch. The sensor device is coupled to the shoe apparatus via one or more connectors of the shoe apparatus. As the sensor device is inserted into the shoe apparatus, features of the shoe apparatus enable alignment of the sensor device with the shoe apparatus and the one or more connectors.

16 Claims, 4 Drawing Sheets

(56) References Cited

U.S. PATENT DOCUMENTS

| | | | |
|---|---|---|---|
| 2010/0228113 A1* | 9/2010 | Solosko | A61B 5/0416 600/382 |
| 2010/0261992 A1* | 10/2010 | Axelgaard | A61B 5/04085 600/391 |
| 2011/0028822 A1* | 2/2011 | Beck | A61B 5/0408 600/386 |
| 2012/0165644 A1* | 6/2012 | Schultz | A61B 5/0416 600/382 |
| 2012/0165645 A1* | 6/2012 | Russell | A61B 5/6804 600/388 |
| 2012/0296174 A1 | 11/2012 | McCombie et al. | |
| 2013/0060115 A1 | 3/2013 | Gehman et al. | |
| 2013/0077263 A1* | 3/2013 | Oleson | A61B 5/6804 361/747 |
| 2015/0087951 A1* | 3/2015 | Felix | A61B 5/0408 600/382 |
| 2015/0094558 A1* | 4/2015 | Russell | A61B 5/0408 600/391 |

* cited by examiner

SELF-ALIGNING DEVICE TO PATCH INTERFACE

BACKGROUND

Field

Embodiments of the present disclosure generally relate to wearable health monitors, and more specifically, an apparatus for aligning and attaching a wearable monitor to a wearable patch.

Description of the Related Art

Wearable health monitors, such as biometric sensors and other measurement instruments, monitor and detect health conditions of a patient. For example, wearable health monitors may be used to detect heart rate data, electrocardiogram data, blood pressure data, blood sugar data, and so on for a patient. This data may be collected over time and presented to health care providers for use in caring for the patient.

A wearable health monitor includes a sensor device and at least one wearable patch. Each wearable patch includes one or more electrodes coupled to the sensor device. Each wearable patch may also include one or more interfacing connector(s), such as studs, so that the sensor device can be selectively removed or optionally reapplied to the wearable patch. The electrodes may also be electrically coupled to the sensor device via one or more wires, such as a lead set.

After a period of time, the wearable patch may need to be replaced by the patient. A new patch is attached to the patient and the sensor device is attached to the patch via the one or more interfacing connector(s). However, on-body application of the sensor device to the wearable patch requires forcibly pushing the sensor device onto the interfacing connector(s). Further, due to the small size of the sensor device, the sensor device may be difficult to align and attach to the one or more wires or the wearable patch. For example, a patient using the wearable health monitor may have limited dexterity, tremors, and so on, making it difficult to align and connect the sensor device to the one or more interfacing connector(s) and the one or more wires.

To enable easier attachment of the sensor device to the patch, the patient may attach the sensor device to the patch before attaching the patch to the user. However, to do so, the patient removes the sensor device from the wearable patch for a longer period of time resulting in a period during which the sensor device is not monitoring the patient.

Accordingly, an improved patch-device interface is needed.

SUMMARY

In one embodiment, an apparatus which includes a shoe having a first end opposite a second end. The shoe includes a base and a raised portion at the first end. An opening is formed through the raised portion. A first sidewall extends laterally from the base. A second sidewall extends laterally from the base and opposite the first sidewall. An electrical connector is disposed through the opening.

In another embodiment, an apparatus is provided which includes a sensor shoe and a sensor device plug. The sensor shoe includes a base having a first end opposite a second end. A raised portion is disposed at the first end of the base. A volume is defined within the raised portion. An opening is formed in the raised portion facing the second end. A first sidewall extends laterally from the base. A second sidewall extends laterally from the base and is opposite the first sidewall. The sensor device plug includes a plug body is positioned in the volume. A plug connector extends from the plug body and through the opening. A lead is coupled to the plug connector.

In another embodiment, an apparatus is provided which includes a wearable patch. One or more electrodes are embedded in the wearable patch. The apparatus also includes a sensor shoe apparatus which includes a base having a first end opposite a second end. A raised portion extends from the first end and has an opening formed therein. A first sidewall extends laterally from the base and is disposed adjacent to the raised portion. A second sidewall extends laterally from the base. The second sidewall is disposed adjacent to the raised portion and opposite the first sidewall. An electrical connector is disposed through the opening. A lead is coupled to the one or more electrodes and the electrical connector.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, may admit to other equally effective embodiments.

To facilitate understanding, identical reference numerals have been used, where possible, to designate identical elements that are common to the figures. It is contemplated that elements and features of one embodiment may be beneficially incorporated in other embodiments without further recitation.

DETAILED DESCRIPTION

Embodiments described herein relate to apparatus and techniques for aligning and coupling a sensor device to a wearable patch. A shoe apparatus is coupled to the wearable patch. The sensor device is coupled to the shoe apparatus via one or more connectors of the shoe apparatus. As the sensor device is inserted into the shoe apparatus, features of the shoe apparatus enable alignment of the sensor device with the shoe apparatus and the one or more connectors.

Figure 1:
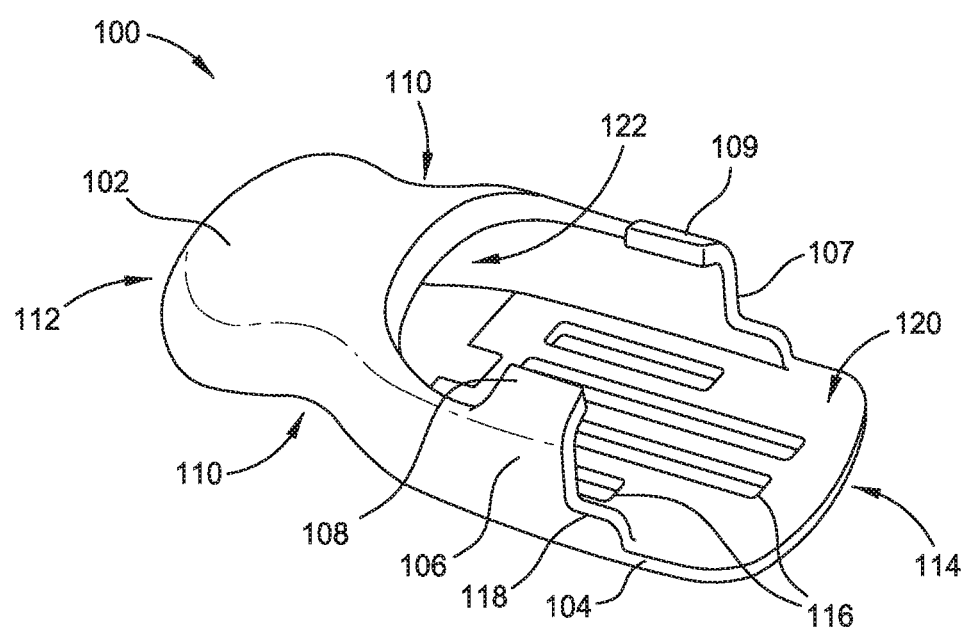
FIG. 1 is a perspective view of a sensor shoe according to one embodiment.

FIG. 1 is a perspective view of a sensor shoe 100 according to one embodiment. The sensor shoe 100 has a first end 112 and a second end 114 opposite the first end 112. The sensor shoe 100 includes a base 104, a raised portion 102, a first sidewall 106, a second sidewall 107, a first locking tab 108, and a second locking tab 109. While the sensor shoe 100 is illustrated having two sidewalls 106 and 107 and two locking tabs 108 and 109, it is contemplated that the sensor shoe 100 is fabricated with one or more sidewalls and one or more locking tabs. In one embodiment, the base 104 includes one or more openings 116 formed therethrough. In one embodiment, the sensor shoe 100 is fabricated from a polymer material, such as an ABS polymer. In one embodiment, the sensor shoe 100 is fabricated from a glass-fiber-filled ABS.

The first sidewall 106 extends laterally from and substantially normal to a top surface 120 of the base 104 of the sensor shoe 100. As the first sidewall 106 extends from the base 104, the first sidewall 106 curves toward the second sidewall 107 to form the first locking tab 108. The second sidewall 107 extends laterally from the base 104 opposite and substantially parallel to the first sidewall 106. As the second sidewall 107 extends from the base 104, the second sidewall 107 curves toward the first sidewall 106 to form the second locking tab 109. In one embodiment, the first locking tab 108 and the second locking tab 109 are separate components of the sensor shoe 100 and are coupled to the respective sidewalls 106 and 107.

One or more alignment tabs 118 extend laterally from the base 104. In one embodiment, the alignment tabs 118 are an extension of the sidewalls 106 and 107. The one or more alignment tabs 118 are coupled to the base 104 via a rounded shoulder. The one or more alignment tabs 118 are substantially parallel to the sidewalls 106 and 107. In one embodiment, one or more finger grooves 110 are formed in the raised portion 102 of the sensor shoe 100. The finger grooves 110 assist the patient to grip the sensor shoe 100 when installing or removing the sensor device therefrom. A texture may be added to a surface of the finger grooves 110 to further improve gripping of the sensor shoe 100.

An opening 122 is defined within the raised portion 102. The opening 122 is positioned between the top of the raised portion 102 and the base 104. The opening 122 is on a side of the raised portion 102 facing the second end 114 of the sensor shoe 100. The opening 122 enables a plug connector (discussed below with respect to FIGS. 3-6) to be inserted therethrough for connecting to a sensor device (not shown).

In operation, the sidewalls 106, 107, the alignment tabs 118, and the locking tabs 108, 109 enable a patient to install the sensor device in the sensor shoe 100 for monitoring health conditions of the patient. The sidewalls 106, 107, the alignment tabs 118, and the locking tabs 108, 109 enable the sensor device to be aligned in the sensor shoe 100 when the sensor device is inserted into the sensor shoe 100. Once inserted, the sidewalls 106, 107 and the locking tabs 108, 109 exert pressure against the sensor device to hold the sensor device in the sensor shoe 100. In one embodiment, the sensor shoe 100 includes a locking mechanism (not shown) to secure the sensor device. In that case, the sensor shoe 100 also includes a release mechanism that is activated to enable removal of the sensor device from the sensor shoe 100. In one embodiment, the sensor shoe 100 provides tactile feedback as confirmation that the sensor device aligned and secured in the sensor shoe 100.

Figure 2:
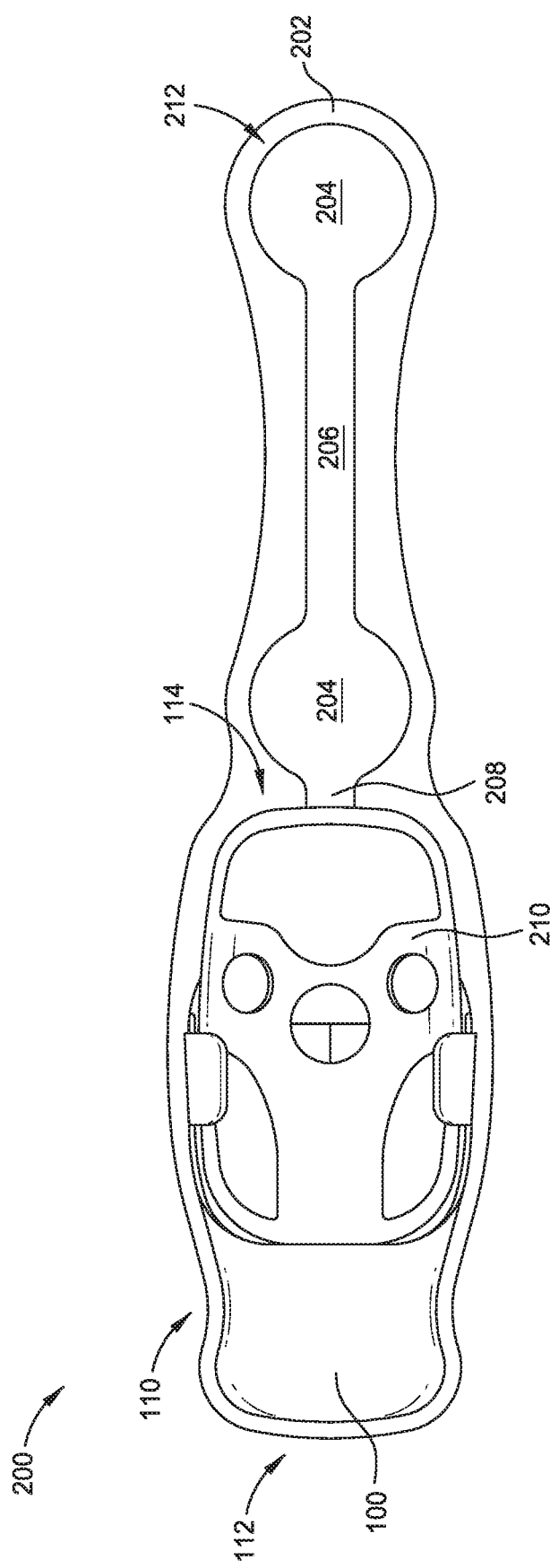
FIG. 2 is a top view of a wearable health monitor according to one embodiment.

FIG. 2 is a top view of a wearable health monitor 200 according to one embodiment. The wearable health monitor 200 includes a wearable patch 202, the sensor shoe 100, and a sensor device 210. In one embodiment, the wearable patch 202 is fabricated from a flexible electrically insulating material. The sensor shoe 100 is adhered to the wearable patch 202 via an adhesive, such as a glue. In one embodiment, a double sided adhesive tape (not shown) is disposed between the wearable patch 202 and the sensor shoe 100. The adhesive or double sided tape maintains a position of the sensor shoe 100 on the wearable patch 202.

The wearable patch 202 includes an electrode assembly 212. The electrode assembly 212 includes one or more electrodes 204 and one or more connectors 206, 208 between the electrodes 204. The electrodes 204 are coupled to each other via a connector 206, 208. The connectors 206, 208 include conductive pathways between each of the electrodes 204. The conductive pathway of each connector 206, 208 is fabricated from a flexible conductive material and is disposed in the wearable patch 202. In one embodiment, the connectors 206, 208 and the electrodes 204 are fabricated from a continuous flexible conductive material disposed in the wearable patch 202. The conductive pathways in the connectors 206, 208 transmit signals between the one or more electrodes 204 to the sensor device 210.

As illustrated in FIG. 2, the electrodes 204 are circular, but other shapes and configurations are contemplated. In one embodiment, the electrodes 204 and the connector 206 are embedded in the wearable patch 202. Thus, when the wearable health monitor 200 is attached to a patient, the wearable patch 202 touches the skin of the patient. The wearable patch 202 is fabricated from a breathable material to facilitate patient comfort. The one or more openings 116 illustrated in FIG. 1 enable air to pass through the base 104 and increase breathability of the sensor shoe 100. The air flow through the openings 116 substantially improves breathability of the wearable patch 202 and thus improves a comfort level of the patient.

When the sensor device 210 is installed in the sensor shoe 100, the electrodes 204 are coupled to the sensor device 210 via a connector 208. The electrodes 204 detect an electrical current in the body of the patient and communicate a corresponding signal to the sensor device 210 via the connectors 206, 208. Each electrode 204 provides a different view of electrical activity in the body of the patient. While two electrodes 204 are illustrated in FIG. 2, it is contemplated that more or less than two electrodes 204 may be embedded in the wearable patch 202 and coupled to the sensor device 210.

Figure 3:
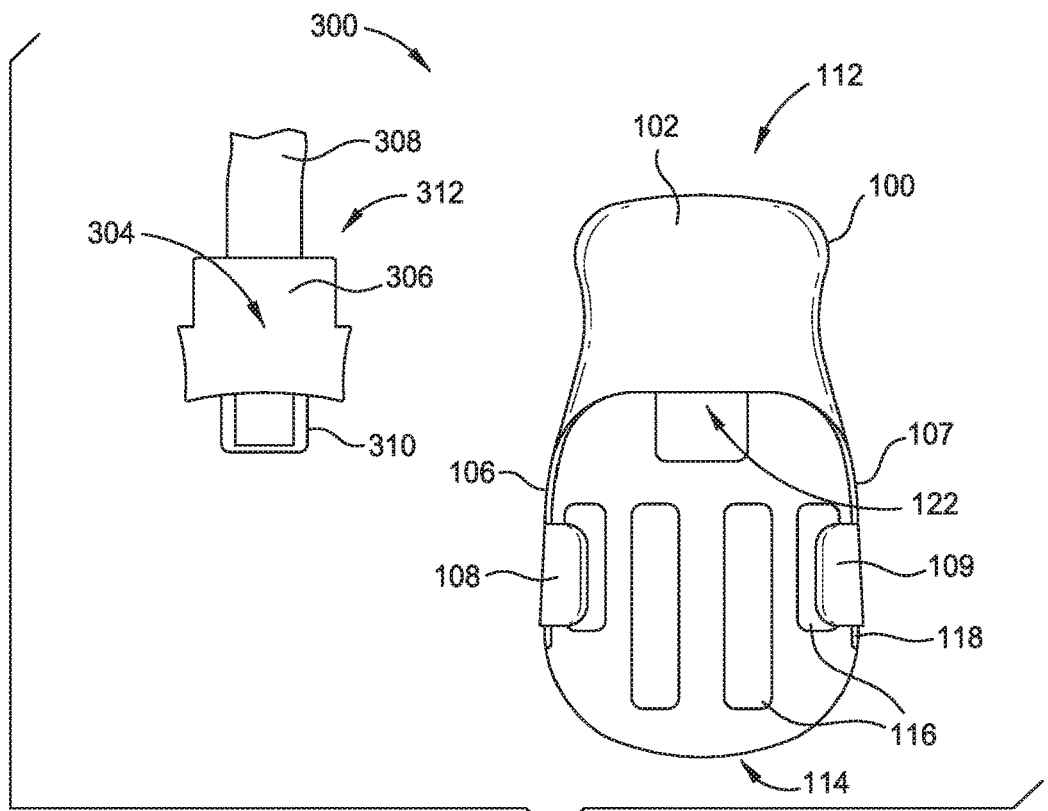
FIG. 3 is a schematic top view of a sensor shoe apparatus according to one embodiment.

FIG. 3 is a schematic top view of a sensor shoe apparatus 300 according to one embodiment. The sensor shoe apparatus 300 includes the sensor shoe 100 and a sensor device plug 312. The sensor shoe 100 corresponds to the sensor shoe 100 described with respect to FIGS. 1 and 2.

The sensor device plug 312 includes a body 306, a plug connector 310, and a lead 308. The lead 308 is coupled to the electrode assembly 212, illustrated in FIG. 2. The lead 308 is fabricated from one or more portions of a flexible conductive material enclosed in the flexible insulating material of the wearable patch 202. In one embodiment, the one or more portions of the flexible conductive material are separated within the flexible insulating material so as to create a separate conductive pathway for each of the one or more portions of flexible conductive material.

In one embodiment, the lead 308 and the electrode assembly 212 forms are fabricated from a continuous flexible conductive material. In one embodiment, the plug connector 310 provides an interface for connecting the sensor device to the lead 308. For example, the plug connector 310 may be a micro USB connector. The lead 308 provides an interface between the sensor device and the electrode assembly 212. In one embodiment, a printed circuit board (PCB) is disposed in the body 306 and the plug connector 310 is rigidly coupled to the PCB and the body 306. The rigid connection between the plug connector 310 and the body 306 enables a user to forcibly insert the sensor device into the sensor shoe 100. In one embodiment, the sensor device 210 is held in the sensor shoe 100 by the plug connector 310.

In operation, the sensor device plug 312 is disposed in the sensor shoe 100 within the raised portion 102. A top surface 304 of the sensor device plug 312 is inserted into a bottom of the opening 122. That is, the sensor device plug 312 is inserted into the raised portion 102 such that the plug connector 310 extends from the opening 122.

In one embodiment, the body 306 is fabricated from the same material as the sensor shoe 100. In another embodiment, the body 306 is fabricated from a similar or different material than the sensor shoe 100. The sensor device plug 312 has an ingress protection (IP) rating of IP67. That is, the sensor device plug 312 substantially prevents dust from entering therein. The sensor device plug 312 also prevents intrusion of liquid when submersed in the liquid at a depth of up to 1 meter for about 30 minutes.

In one embodiment, the sidewalls 106 and 107 of the sensor shoe 100 are tapered from the second end 114 of the sensor shoe 100 to the first end 112 of the sensor shoe 100. That is, a width between the sidewalls 106 and 107 gradually decreases from the second end 114 toward the first end 112. In another embodiment, which can be combined with one or more embodiments described above, a thickness of the sidewalls 106 and 107 may be tapered from the first end 112 toward the second end 114. For example, a thickness of the sidewalls 106 and 107 may decrease from the first end 112 toward the second end 114. While the sensor shoe apparatus 300 is illustrated as two components in FIG. 3, it is contemplated that the sensor shoe apparatus 300 is manufactured as a unitary apparatus including the sensor shoe 100 and the sensor device plug 312.

Figure 4:
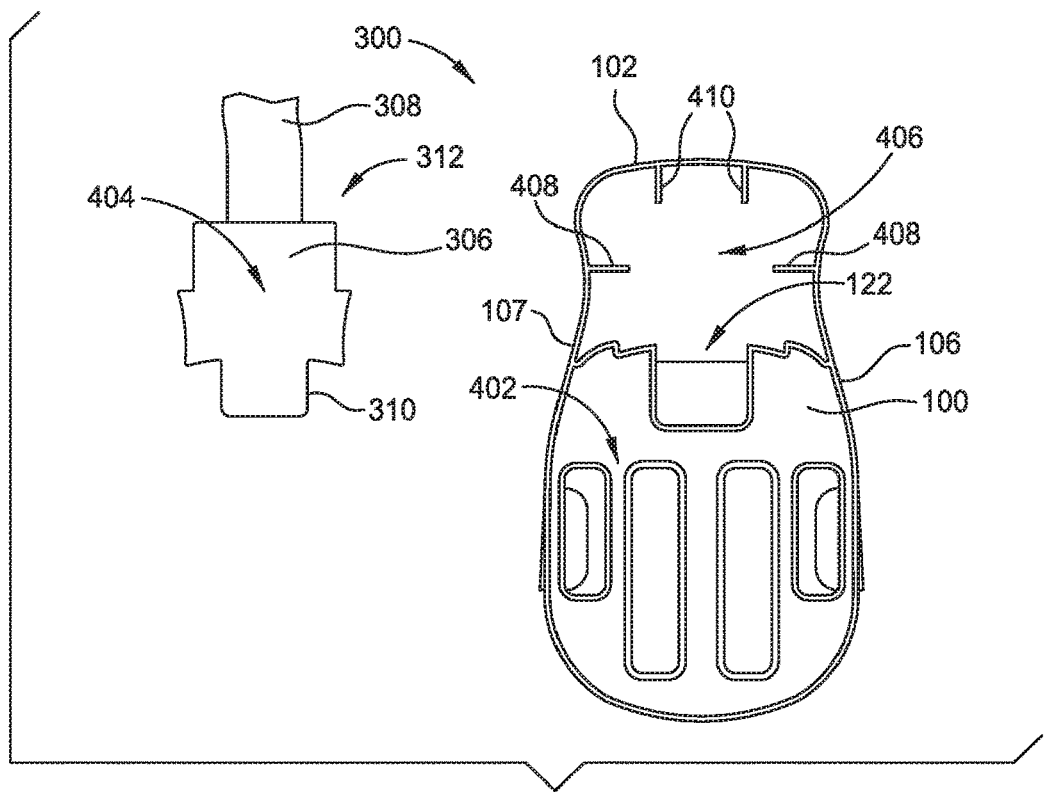
FIG. 4 is a schematic bottom view of the sensor shoe apparatus according to one embodiment.

FIG. 4 is a schematic bottom view of the sensor shoe apparatus 300 according to one embodiment. The sensor shoe 100 includes a volume 406 formed in the raised portion 102. A shape of the sensor device plug 312 is substantially the same as a shape of the volume 406. Thus, when the sensor device plug 312 is inserted in the sensor shoe 100, the sensor device plug substantially fills the volume 406 and a bottom surface 404 of the sensor device plug 312 is substantially co-planar with a bottom surface 402 of the sensor shoe 100. When the sensor device plug is inserted in the volume 406, the plug connector 310 passes through the opening 122.

One or more first support members 408 extend laterally from each of the sidewalls 106 and 107. The one or more first support members 408 extending from the first sidewall 106 are substantially parallel to the one or more first support members 408 extending from the second sidewall 107. One or more second support members 410 extend laterally from the first end 112 of the sensor shoe 100. The one or more second support members 410 are substantially perpendicular to the one or more first support members 408. The one or more second support members 410 are substantially parallel to the first sidewall 106 and the second sidewall 107. Each of the first support members 408 and the second support members 410 extend into the volume 406. The first support members 408 and the second support members 410 provide support to the sensor device plug 312 when inserted into the sensor shoe 100. The first support members 408 and the second support members 410 enable alignment of the plug connector 310 with the opening 122 when the sensor device plug 312 is inserted into the volume 406. When the sensor device plug 312 is inserted in the volume 406, the first support members 408 and the second support members 410 hold the sensor device plug 312 in the volume 406 by exerting a force on the sides of the sensor device plug 312.

Figure 5:
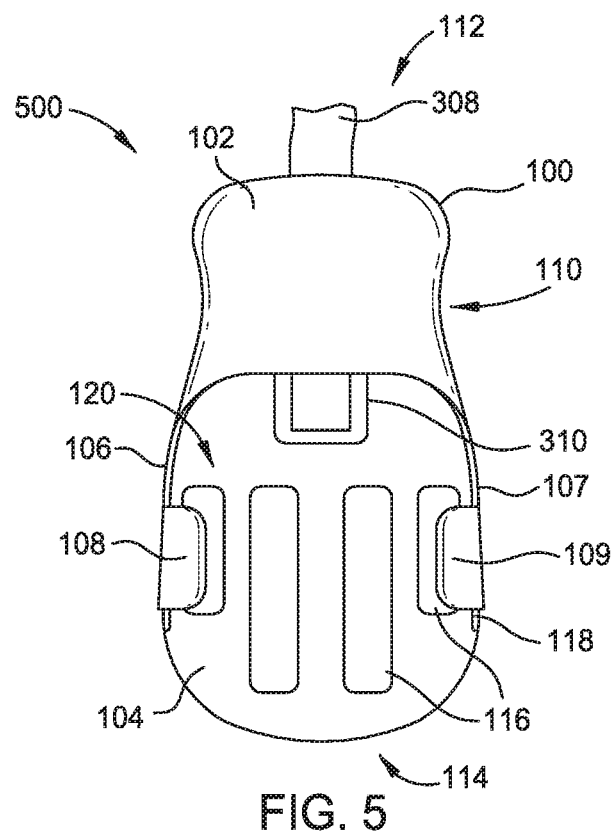
FIG. 5 is a schematic view of the assembled sensor shoe apparatus according to one embodiment.

FIG. 5 is a schematic view of the assembled sensor shoe apparatus 500 according to one embodiment. As illustrated, the assembled sensor shoe apparatus 500 includes the sensor shoe 100 and the sensor device plug 312 extending from the volume 406 (illustrated in FIG. 4) within the raised portion 102. When the sensor device plug 312 is in the volume 406, the plug connector 310 extends through the opening 122 (illustrated in FIGS. 1, 3, and 4) toward the second end 114 of the sensor shoe 100. When assembled, the plug connector 310 extends through the opening 122 substantially parallel to the sidewalls 106 and 107.

As the sensor device is inserted into the sensor shoe 100 and moved toward the first end 112 of the sensor shoe 100, the locking tabs 108 and 109 and the tapered sidewalls 106, 107 align the sensor device with the plug connector 310. Thus, as the sensor device is inserted into the sensor shoe 100 and moved toward the first end 112, the plug connector 310 is aligned with and inserted into a corresponding connector of the sensor device.

Figure 6:
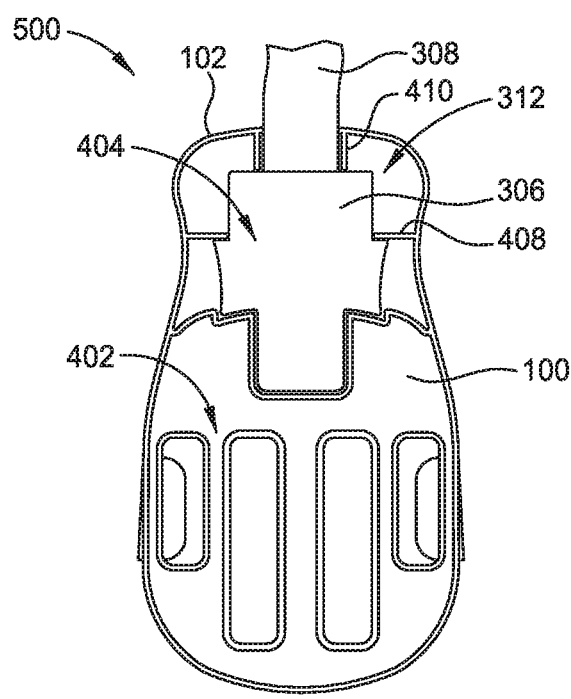
FIG. 6 is a bottom view of the assembled sensor shoe apparatus according to one embodiment.

FIG. 6 is a bottom view of the assembled sensor shoe apparatus 500 according to one embodiment. The sensor device plug 312 is positioned in the volume 406 illustrated in FIG. 4 between the support members 408 and 410. The sensor device plug 312 substantially fills the volume 406. In one embodiment, the lead 308 extends from the sensor shoe 100 between the second support members 410.

Embodiments of the present disclosure provide a sensor shoe for mounting a sensor device on a wearable patch. The sensor shoe enables alignment of the sensor device as the sensor device is inserted into the sensor shoe. The sensor shoe also protects the sensor device and holds the sensor device in place on the wearable patch and the patient. Minimal force can be used to insert the sensor device into the sensor shoe. The sensor shoe enables the sensor device to be removed from the wearable patch so that the sensor device can be reused by the same patient or a different patient with a new patch and sensor shoe.

While the foregoing is directed to embodiments of the present disclosure, other and further embodiments of the disclosure may be devised without departing from the basic scope thereof, and the scope thereof is determined by the claims that follow.

What is claimed is:
1. A sensor shoe, comprising:
   a base having a first end opposite a second end, and configured to attach to a wearable patch fabricated from a flexible material and comprising one or more embedded electrodes;
   a raised portion at the first end having an opening facing the second end;
   a first sidewall extending laterally from the base;
   a second sidewall extending laterally from the base and opposite the first sidewall, wherein a distance between the first sidewall and the second sidewall is tapered such that the distance is narrower at a first point closer to the first end compared with a second point closer to the second end;
   one or more alignment tabs extending laterally from the base and extending from at least one of the first sidewall or the second sidewall;
   one or more holes formed through the base to the wearable patch, the holes configured to allow airflow through the base to the wearable patch; and an electrical connector disposed through the opening and configured to electrically couple a removable biometric sensor device with the one or more embedded electrodes.

2. The sensor shoe of claim 1, wherein a thickness of the first sidewall and the second sidewall is tapered from the first end toward the second end.

3. The sensor shoe of claim 1, wherein the first sidewall and the second sidewall are substantially perpendicular to the base.

4. The sensor shoe of claim 3, further comprising:
one or more grooves formed in the raised portion.

5. The sensor shoe of claim 3, further comprising:
a first locking tab extending from the first sidewall toward the second sidewall; and
a second locking tab extending from the second sidewall toward the first locking tab.

6. An apparatus, comprising:
a sensor shoe, comprising:
a base having a first end opposite a second end and configured to attach to a wearable patch fabricated from a flexible material and comprising one or more embedded electrodes;
a raised portion defining a volume therein, the raised portion disposed at the first end of the base;
an opening formed in the raised portion facing the second end;
a first sidewall extending laterally from the base;
a second sidewall extending laterally from the base and opposite the first sidewall, wherein a distance between the first sidewall and the second sidewall is tapered such that the distance is narrower at a first point closer to the first end compared with a second point closer to the second end;
one or more alignment tabs extending laterally from the base and extending from at least one of the first sidewall or the second sidewall;
one or more holes formed through the base to the wearable patch, the holes configured to allow airflow through the base to the wearable patch; and
a sensor device plug configured to electrically couple a removable biometric sensor device with the one or more embedded electrodes, comprising:
a plug body positioned in the volume;
a plug connector extending from the plug body and through the opening; and
a lead coupled to the plug connector.

7. The apparatus of claim 6, wherein a thickness of the first sidewall and the second sidewall is tapered from the first end toward the second end.

8. The apparatus of claim 6, wherein the first sidewall and the second sidewall are substantially perpendicular to the base.

9. The apparatus of claim 8, further comprising:
one or more grooves formed in the raised portion.

10. The apparatus of claim 8, further comprising:
a first locking tab extending from the first sidewall toward the second sidewall; and
a second locking tab extending from the second sidewall toward the first locking tab.

11. An apparatus, comprising:
a wearable patch fabricated from a flexible material;
one or more electrodes embedded in the wearable patch; and
a sensor shoe apparatus, the sensor shoe apparatus comprising:
a base having a first end opposite a second end and configured to attach to the wearable patch;
a raised portion extending from the first end having an opening facing the second end;
a first sidewall extending laterally from the base and disposed adjacent to the raised portion;
a second sidewall extending laterally from the base, the second sidewall disposed adjacent to the raised portion and opposite the first sidewall, wherein a distance between the first sidewall and the second sidewall is tapered such that the distance is narrower at a first point closer to the first end compared with a second point closer to the second end;
one or more alignment tabs extending laterally from the base and extending from at least one of the first sidewall or the second sidewall;
one or more holes formed through the base to the wearable patch, the holes configured to allow airflow through the base to the wearable patch; and
an electrical connector disposed through the opening and configured to electrically couple a removable biometric sensor device with the one or more embedded electrodes.

12. The apparatus of claim 11, wherein the sensor shoe apparatus is adhered to the wearable patch via an adhesive.

13. The apparatus of claim 11, wherein the first sidewall and the second sidewall are substantially perpendicular to the base.

14. The apparatus of claim 11, wherein the one or more electrodes embedded in the wearable patch comprises a plurality of electrodes, and wherein each electrode of the plurality of electrodes is electrically coupled to at least one other electrode of the plurality of electrodes.

15. The apparatus of claim 11, further comprising:
a first locking tab extending from the first sidewall toward the second sidewall; and
a second locking tab extending from the second sidewall toward the first locking tab.

16. The sensor shoe of claim 1, further comprising:
a first locking tab extending from the first sidewall toward the second sidewall; and
a second locking tab extending from the second sidewall toward the first locking tab,
wherein the one or more embedded electrodes comprises a plurality of electrodes, and wherein each electrode of the plurality of electrodes is electrically coupled to at least one other electrode of the plurality of electrodes.

* * * * *